(12) United States Patent
Kameoka

(10) Patent No.: US 6,937,324 B2
(45) Date of Patent: Aug. 30, 2005

(54) COMBINED ANALYZING APPARATUS

(75) Inventor: Masaru Kameoka, Osaka (JP)

(73) Assignee: Nippon Pastec Co., Ltd., Osaka (JP)

(*) Notice: Subject to any disclaimer, the term of this patent is extended or adjusted under 35 U.S.C. 154(b) by 406 days.

(21) Appl. No.: 10/214,358

(22) Filed: Aug. 8, 2002

(65) Prior Publication Data

US 2003/0184733 A1 Oct. 2, 2003

(30) Foreign Application Priority Data

Mar. 29, 2002 (JP) ........................................ 2002-095076

(51) Int. Cl.[7] ........................ G01N 21/00; G01B 9/02; G01J 5/02
(52) U.S. Cl. ..................... 356/73; 356/451; 250/339.08; 250/343
(58) Field of Search .............. 356/73, 451; 250/339.08, 250/343, 281–288

(56) References Cited

U.S. PATENT DOCUMENTS

| | | |
|---|---|---|
| 5,313,061 A | 5/1994 | Drew et al. |
| 5,440,120 A | 8/1995 | Roberts et al. |
| 5,811,059 A | 9/1998 | Genovese et al. |
| 5,942,440 A | 8/1999 | Dooley et al. |
| 6,351,983 B1 | 3/2002 | Haas et al. |

FOREIGN PATENT DOCUMENTS

EP 0 995 988 4/2000

OTHER PUBLICATIONS

Tania A. Sasaki et al., "Gas Chromatography with Fourier Transform Infrared and Mass Spectral Detection", Journal of Chromatography A, Elsevier Science, NL, vol. 842, no. 1–2, May 21, 1999, pp. 341–349.
N. Ragunathan et al., "Gas Chromatography with Spectroscopic Detectors", Journal of Chromatography A, Elseveir Science, NL, vol. 856, no. 1–2, Sep. 24, 1999, pp. 349–397.

*Primary Examiner*—Gregory J. Toatley, Jr.
*Assistant Examiner*—Amanda Merlino
(74) *Attorney, Agent, or Firm*—Wenderoth, Lind & Ponack, L.L.P.

(57) ABSTRACT

A combined analyzing apparatus includes (i) a front end unit including a photoacoustic spectroscope that takes a gas sample inside and analyzes the gas sample by a photoacoustic spectroscopy, (ii) a light analyzing apparatus that takes the analyzed gas sample inside and analyzes the gas sample based on a change of light which is transmitted through the gas sample, and (iii) a mass analyzing apparatus that further takes the analyzed gas sample inside and analyzes a mass of an ingredient of the gas sample. The combined analyzing apparatus also includes (iv) a battery that supplies the front end unit, and the light analyzing apparatus and the mass analyzing apparatus with electric power source, and (v) a portable case that houses the front end unit, the light analyzing apparatus, the mass analyzing apparatus and the battery.

18 Claims, 7 Drawing Sheets

COMBINED ANALYZING APPARATUS

BACKGROUND OF THE INVENTION (1) Field of the Invention

The present invention relates to a combined analyzing apparatus that analyzes a gas sample using a light analyzing apparatus and a mass analyzing apparatus.

(2) Description of the Related Art

Various types of analyzing apparatus such as a light analyzing apparatus like a Fourier transform infrared spectrophotometer (FTIR) that takes a gas sample inside and analyzes the gas sample based on a change of light which is transmitted through the gas sample and a mass analyzing apparatus that analyzes a mass of an ingredient included in the gas sample have been proposed in the prior art, and these analyzing apparatus are respectively used for different types of gas samples and for different purposes of the analyses.

Also, as terrorism attacks and crimes using chemical weapons (NBC weapons) such as a toxic gas have increased in recent years, an immediate analysis of an unknown gas in all aspects is required on the site where the toxic gas is being sampled.

Furthermore, global environmental pollutants such as a greenhouse gas, an environmental hormone and a soil contaminant have also been on the rise in these years, and therefore, an immediate on-site analysis of an unknown gas is required in terms of a global environment, too.

However, at least a light analyzing apparatus and a mass analyzing apparatus are usually required on the above-mentioned site, and there is a problem that it takes a lot of time and trouble with carrying and assembling these analyzing apparatus.

SUMMARY OF THE INVENTION

Accordingly, the object of the present invention is, in the light of the above-mentioned problem, to provide an easy-to-carry combined analyzing apparatus that is a combination of at least a light analyzing apparatus and a mass analyzing apparatus.

In order to achieve the above object, the present invention includes a light analyzing apparatus that takes a gas sample inside and analyzes the gas sample based on a change of light which is transmitted through the gas sample; a mass analyzing apparatus that takes the analyzed gas sample inside and analyzes a mass of an ingredient of the gas sample; and a portable case that houses at least the light analyzing apparatus and the mass analyzing apparatus. For example, the light analyzing apparatus is a Fourier transform infrared spectrophotometer, and the mass analyzing apparatus is a time of flight mass spectrometer.

Accordingly, since the light analyzing apparatus and the mass analyzing apparatus are housed in the portable case, it is easy to carry them.

Also, an outlet of the light analyzing apparatus for taking out the gas sample which has been taken inside may be connected approximately face to face with an intake of the mass analyzing apparatus for taking the gas sample inside so that the gas sample is led from the light analyzing apparatus straight to the mass analyzing apparatus without branching off.

Accordingly, since the entire apparatus is downsized by shortening a duct member that leads the gas sample from the light analyzing apparatus to the mass analyzing apparatus, it becomes easier to carry the apparatus.

Also, the light analyzing apparatus may include a cell container that is filled with the gas sample in order to transmit light through the gas sample, and the mass analyzing apparatus may be arranged directly in contact to the cell container of the light analyzing apparatus.

Accordingly, since the entire apparatus is downsized as in the case of the above, it becomes further easier to carry the apparatus.

Also, the combined analyzing apparatus may include a front end analyzing apparatus in the portable case that takes the gas sample inside and analyzes the gas sample before the light analyzing apparatus and the mass analyzing apparatus analyze the gas sample. For example, the front end analyzing apparatus is a photoacoustic spectroscope (PAS) that analyzes the gas sample by a photoacoustic spectroscopy.

Accordingly, since the front end analyzing apparatus, the light analyzing apparatus and the mass analyzing apparatus are housed in the case, an analysis range of the gas sample can be expanded.

Also, an outlet of the front end analyzing apparatus for taking out the gas sample which has been taken inside may be connected approximately face to face with an intake of the light analyzing apparatus for taking the gas sample inside so that the gas sample is led from the front end analyzing apparatus straight to the mass analyzing apparatus via the light analyzing apparatus without branching off.

Accordingly, upsizing of the entire apparatus can be restrained by shortening a duct member that leads the gas sample from the front end analyzing apparatus to the light analyzing apparatus.

Furthermore, the combined analyzing apparatus may further include a digital processing unit operable to perform quantitative analysis based on signals which are outputted from the light analyzing apparatus, and the mass analyzing apparatus and the front end analyzing apparatus, and display a chart indicating an analysis result by the light analyzing apparatus, a chart indicating an analysis result by the mass analyzing apparatus and a chart indicating an analysis result by the front end analyzing apparatus.

Accordingly, since the analysis results of the three analyzing apparatus are displayed on the display of the digital processing unit, a user can understand the analysis results easily, that is, the usability of the apparatus is improved.

BRIEF DESCRIPTION OF THE DRAWINGS

These and other objects, advantages and features of the invention will become apparent from the following description thereof taken in conjunction with the accompanying drawings that illustrate a specific embodiment of the invention. In the Drawings.

DESCRIPTION OF THE PREFERRED EMBODIMENT(S)

The following is an explanation of the combined analyzing apparatus according to the embodiment of the present invention with reference to figures.

Figure 1:
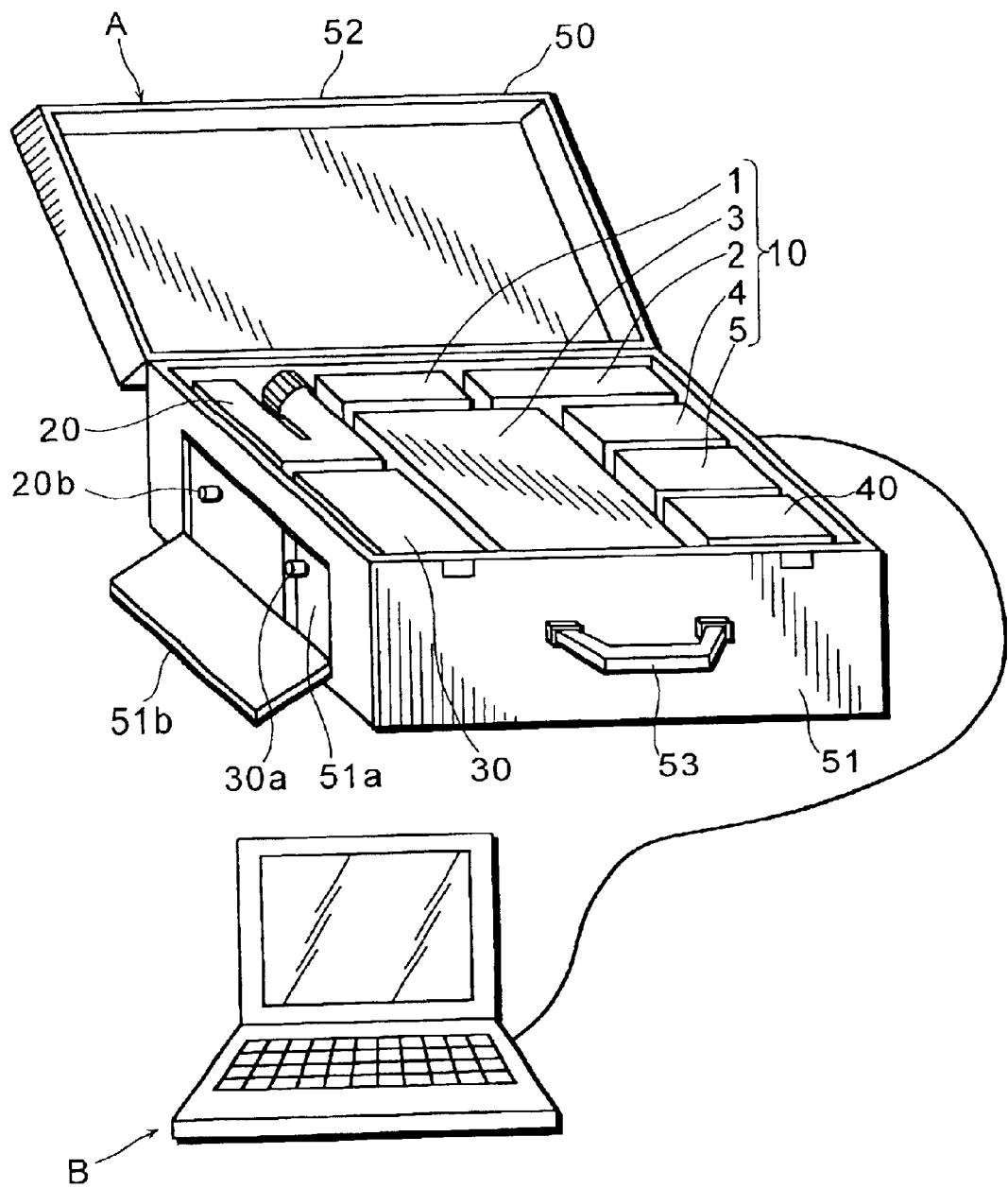
FIG. 1 is an external view of an arrangement of the embodiment of the present invention.

FIG. 1 is an external arrangement view showing the external appearance of the combined analyzing apparatus.

This combined analyzing apparatus includes an analyzing equipment unit A that takes a gas sample inside and outputs a signal corresponding to an ingredient of the gas sample and an operational processing unit B such as a notebook computer that performs operational processing based on the signal outputted from the analyzing equipment unit A and displays the analysis results quantitatively.

The analyzing equipment unit A includes a Fourier transform infrared spectrophotometer (hereinafter referred to as "FTIR") 10 that takes a gas sample to be analyzed inside and analyzes the gas sample based on a spectrum change of infrared rays which are transmitted through the gas sample, a mass spectrometer (hereinafter referred to as "MS") 20 that takes a gas sample inside and analyzes a mass of an ingredient included in the gas sample, a front end unit 30 including a photoacoustic spectroscope and an X-ray analyzing apparatus, etc., a battery 40 that supplies the FTIR 10, the MS 20 and the front end unit 30 with power, and a portable case 50 that houses the FTIR 10, the MS 20, the front end unit 30 and the battery 40. Here, the battery 40 includes a secondary or fuel battery, for example.

Figure 2:
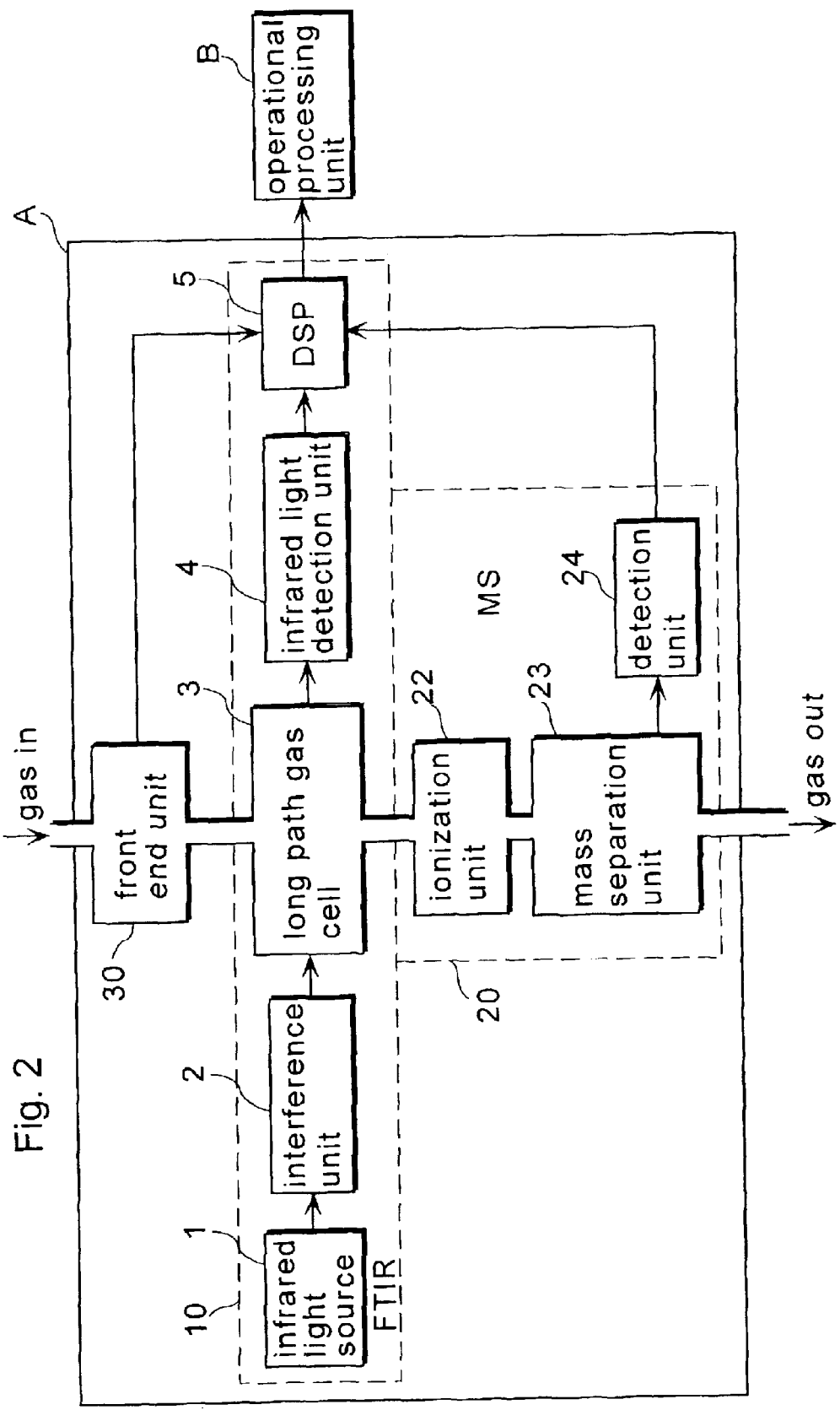
FIG. 2 is a functional block diagram of the present embodiment.

FIG. 2 is a functional block diagram of the combined analyzing apparatus.

As shown in FIG. 2, the FTIR 10 includes an infrared light source 1 that outputs infrared rays, an interference unit 2 including a Michelson's interferometer for interfering the infrared rays outputted from the infrared light source 1, a long path gas cell 3 which is a cell container that takes a gas sample inside so as to fill the container and transmits the infrared rays outputted from the interference unit 2 through the gas sample along the long path, an infrared light detection unit 4 that detects intensity of the infrared rays and a DSP (digital signal processor) 5 that performs a Fourier transform of at least the result outputted from the infrared light detection unit 4 and outputs it to the operational processing unit B.

The MS 20 is a time of flight mass spectrometer that ionizes ingredients included in a gas and lets them fly, and measures a mass of each ingredient based on a flying time to a certain distance. The MS 20 includes an ionization unit 22 that ionizes ingredients of a gas sample in a vacuum and emits the ion ingredients in a certain direction by accelerating them with the application of an electric field, a mass separation unit 23 that lets fly the emitted ion ingredients in a vacuum so as to separate them into each ingredient depending upon a difference in a flying time per mass, and a detection unit 24 that detects each separated ion ingredient.

Figure 3:
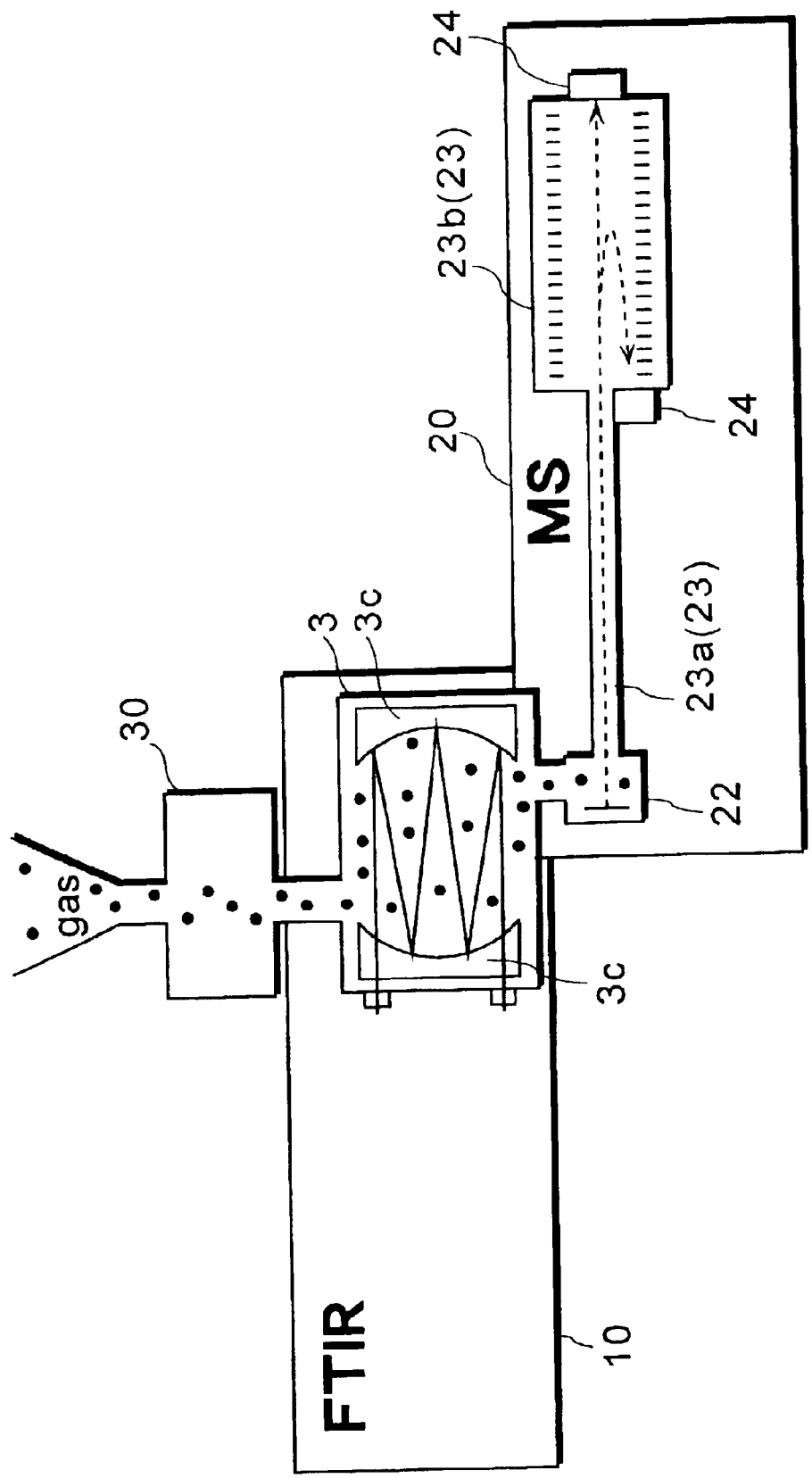
FIG. 3 is an internal structure of a long path gas cell and a mass spectrometer (MS) of the present embodiment.

FIG. 3 is an internal structure of the long path gas cell 3 and the MS 20.

A plurality of reflecting mirrors 3c that reflect the infrared rays outputted from the interference unit 2 are arranged inside the long path gas cell 3, and the number and positions of the reflecting mirrors 3c are set depending upon a distance in which the infrared rays are transmitted through the gas sample, that is, a light path length. The light path length is several (cm)~dozens (m), and is determined depending upon the amount and flow rate of the gas sample. When the gas sample is very little, the light path length is set at about 20 m, for example.

The mass separation unit 23 of the MS 20 includes a drift tube 23a for passing through the ion ingredients emitted from the ionization unit 22, and an ion reflector 23b that makes an electric field gradient so that the strength is applied in the direction opposite to the flying direction of the ion ingredients which pass through the drift tube 23a. Also, the MS 20 includes two detection units 24, and one detection unit is placed in the vicinity of the connecting portion between the drift tube 23a and the ion reflector 23b and another is placed at one end of the ion reflector 23b opposite to the drift tube 23a.

Even if the masses of the ion ingredients emitted from the ionization unit 22 are approximately same, they may sometimes become less resolvable due to differences in a flying time caused by variations in the initial position and initial speed, etc. However, with the ion reflector 23b being placed, the higher-speed ion ingredients which have passed through the drift tube 23a go a long way round, that is, go into the depths of the ion reflector 23b against the above-mentioned electric field gradient, bounce off and are detected by the detection unit 24 which is placed near the drift tube 23a. On the other hand, the lower-speed ion ingredients which have passed through the drift tube 23a take a shortcut, that is, bounce off without going into the depths of the ion reflector 23b and are detected by the detection unit 24 which is placed near the drift tube 23a, as in the case of the high-speed ion ingredients as mentioned above. As a result, the time which is detected by the detection unit 24, that is, the flying time of the ion ingredients with the approximately same mass can be almost same, and therefore these ion ingredients become more resolvable even if there are variations in the initial speed, etc.

The MS 20, that is, a time of flight mass spectrometer as mentioned above, has no upper limit of a mass to be measured in principle, and therefore can measure a high polymer such as protein including tens of thousands~hundreds of thousands molecules. In addition, as the MS 20 is compact overall, its operation and maintenance are easy, and its measuring time is short, it allows easy processing of many samples. Furthermore, as most of the generated ion ingredients reach the detection unit 24, the MS 20 has a good sensitivity and is suitable for a micro analysis.

The front end unit 30 is a unit for taking a gas sample inside and analyzing it. It is, for example, a photoacoustic spectroscope that analyzes a gas sample by a photoacoustic spectroscopy, an X-ray analyzing device that analyzes an X-ray emitted from a gas sample, a radioactive analyzing device that analyzes radioactivity, or a gas sensor that detects a certain gas such as gaseous chlorine and hydrogen sulfide.

When the front end unit 30 is a photoacoustic spectroscope, it includes a gas cell for taking a gas sample inside, a light source unit for applying light to the gas sample in the gas cell and a microphone which is a detection unit for detecting a sound from the gas cell.

The above-mentioned gas sensor includes a ceramic sensor that detects a gas using ceramics, an electrochemical sensor that detects a gas by an electrochemical action, an optical sensor that detects a gas by an optical action, etc. Furthermore, the electrochemical sensor is, for example, a gelled electrolytic sensor that detects a certain ingredient in a gas sample by making the gas sample react on an electrode and measuring the electrode reaction current through a gelled electrolyte.

Note that the front end unit 30 may be a combination of the above-mentioned photoacoustic spectroscope, X-ray analyzing device, radioactive analyzing device and gas sensor.

In the analyzing equipment unit A, a gas sample is first taken into the front end unit 30 so as to be analyzed by the front end unit 30, and then taken into the long path gas cell 3 so as to be analyzed by the FTIR 10. The gas sample which is analyzed by the FTIR 10 is further taken into the ionization unit 22 and the mass separation unit 23 of the MS 20, and as a result, the mass analysis based on the time of flight is performed, as mentioned above.

As mentioned above, as the analyzing apparatus according to the present embodiment includes not only the FTIR 10 and the MS 20, but also the front end unit 30, it expands a range of gas samples that it can analyzes.

Also, the MS 20 analyzes a destroyed gas sample, that is, an ionized ingredient of the gas sample, while the FTIR 10 and the front end 30 analyze the undestroyed gas sample. In other words, according to the present invention, as the gas sample is analyzed by the MS 20 after it is analyzed by the FTIR 10 and the front end unit 30, the gas sample can be analyzed more accurately than it is analyzed by the MS 20 before it is analyzed by the FTIR 10 and the front end unit 30.

Not only the output signal from the infrared light detection unit 4 but also the output signals from the detection unit 24 of the MS 20 and from the microphone of the front end unit 30 are inputted to the DSP 5 of the FTIR 10. The DSP 5 performs the processing of these signals and then outputs them to the operational processing unit B.

The operational processing unit B performs operational processing based on the output signals from the DSP 5 of the analyzing equipment unit A and then displays the results on a display.

Figure 4:
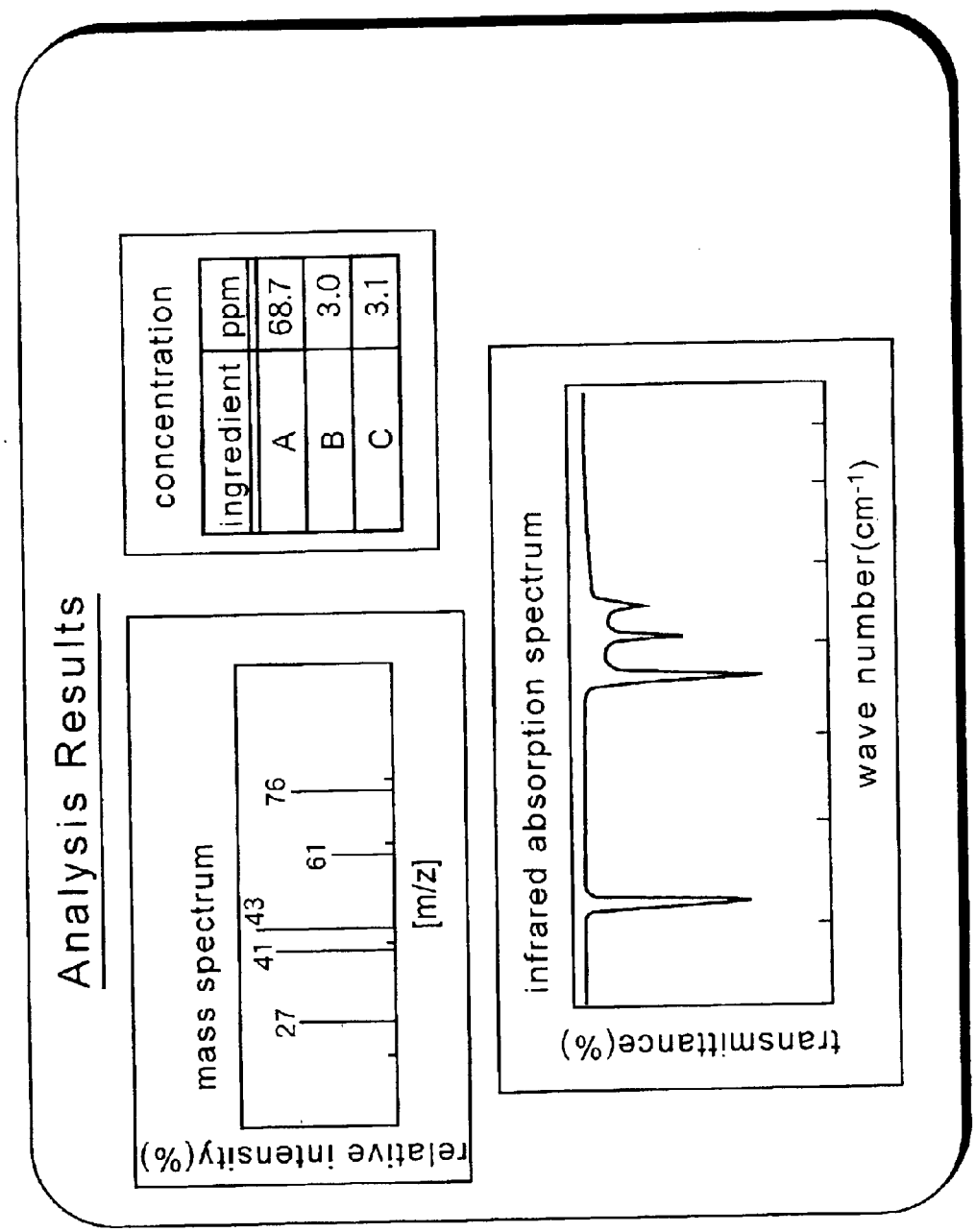
FIG. 4 is a screen display of an operational processing unit of the present embodiment.

FIG. 4 is a screen display of the operational processing unit B indicating the above results.

On the display of the operational processing unit B, the following are displayed at the same time: an infrared absorption spectrum indicating the analysis result of the FTIR 10, a mass spectrum indicating the analysis result of the MS 20, and a table indicating a concentration of each ingredient included in the gas sample, that is, the analysis result by a photoacoustic spectroscopy, if the front end unit 30 is the photoacoustic spectroscope. Likewise, when the front end unit 30 is a X-ray analyzing device, a radioactive analyzing device, or a gas sensor, a table indicating the detection result of the X-ray emitted from the gas sample, a table indicating the analysis result by the radioactive analyzing device, or a table indicating a concentration of a gas detected by the gas sensor, respectively, is displayed on the above-mentioned display.

As a result, according to the combined analyzing apparatus of the present embodiment, as respective results of the three analyzing apparatus can be displayed on the display of the operational processing unit B, the analysis results of the gas sample can be more simple and easy to understand and thus more user-friendly. Also, as the analysis results are displayed on the display of the operational processing unit B all together at one time, a user can easily understand the analysis results as a whole.

The case 50 includes a housing 51 of an approximately rectangular box with one side open and a lid 52 which is mounted on the housing 51 to open and close flexibly with a hinge to bridge a gap between them, and a handle 53 for carrying the analyzing equipment unit A is mounted on the outer side wall of the housing 51. Also, an opening window 51a which faces both inside and outside the housing 51 is created on one side of the housing 51 adjacent to the side on which the handle 53 is mounted and an opening/closing door 51b for opening and closing the opening window 51a is mounted with a hinge or the like.

Here, according to the combined analyzing apparatus of the present embodiment, the above-mentioned FTIR 10, MS 20 and front end unit 30 are housed in the portable case 50 for easy carrying.

Also, according to the combined analyzing apparatus of the present embodiment, as the long path gas cell 3 of the FTIR 10 is arranged close to the MS 20 and the front end unit 30, each analyzing apparatus analyzes a gas sample in the order of the front end unit 30→the FTIR 10→the MS 20 by running the gas sample through them without separation, as mentioned above.

Figure 5:
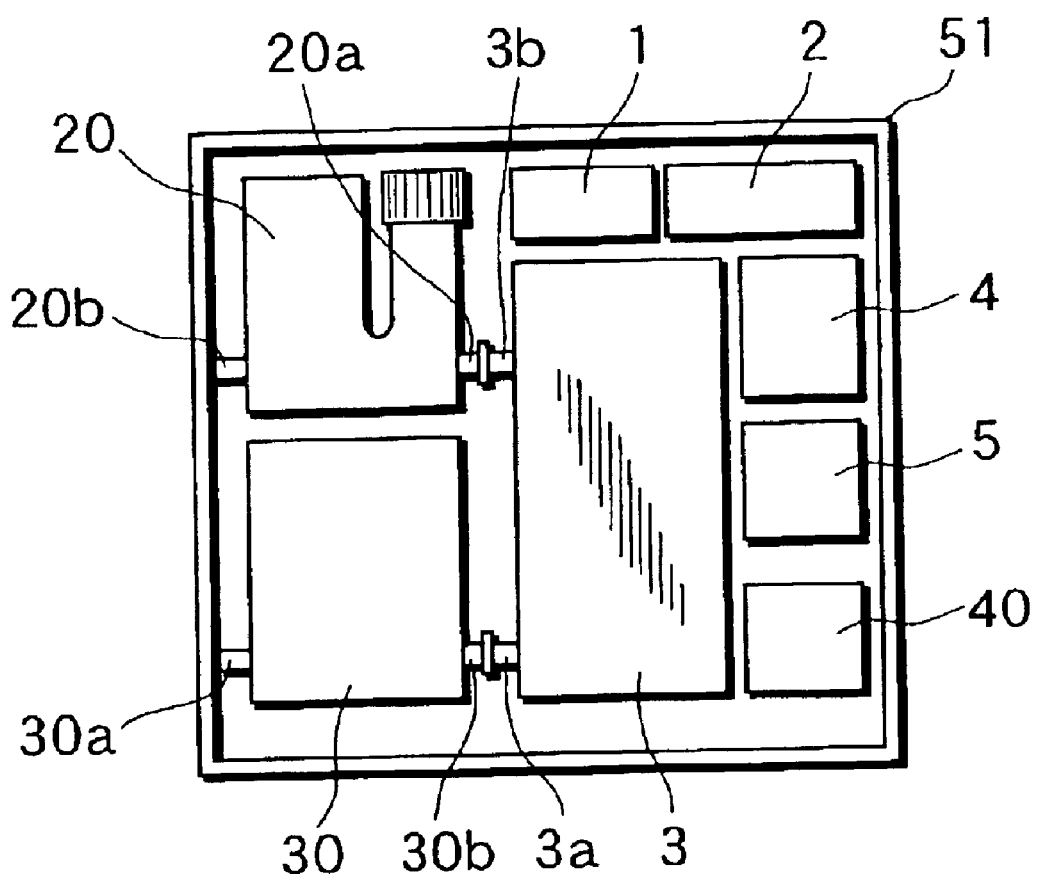
FIG. 5 is a layout in an analyzing equipment unit according to the present embodiment.

FIG. 5 is a layout of the above-mentioned analyzing apparatus arranged in the housing 51 of the case 50.

An intake 30a of the front end unit 30 for taking a gas sample inside is housed in the housing 51 so as to face to a part of the opening window 51a as shown in FIG. 1, and an outlet 20b of the MS 20 for taking the gas sample outside is housed in the housing 51 so as to face to the other part of the opening window 51a likewise as shown in FIG. 1. Also, an outlet 30b of the front end unit 30 for taking the gas sample outside is mounted at the opposite side of the intake 30a, and an intake 20a of the MS 20 for taking the gas sample inside is mounted at the opposite side of the outlet 20b.

An intake 3a for taking the gas sample inside and an outlet 3b for taking it outside are mounted on one side of the long path gas cell 3 of the FTIR 10. The intake 3a and outlet 3b of the long path gas cell 3 are arranged close to the front end unit 30 and the MS 20 approximately face to face with the outlet 30b of the front end unit 30 and the intake 20a of the MS 20, respectively. The infrared light source 1, the interference unit 2, the infrared light detection unit 4, the DSP 5 and the battery 40 are arranged along the sides of the long path gas cell 3 except the side where the long path gas cell 3 approximately faces to the MS 20 and the front end unit 30.

As mentioned above, as the long path gas cell 3 is arranged close to the MS 20 and the front end unit 30 by approximately facing their respective intakes and outlets to one another and the gas sample is run through them without being separated, the entire length of the duct for taking the gas sample into each analyzing apparatus can be shortened. As a result, downsizing of the entire combined analyzing apparatus can be realized by making the analyzing equipment unit A smaller, and therefore it can be easy-to-carry.

Here, the MS 20 and the front end unit 30 may be arranged so as to be in close contact with the long path gas cell 3, the intake 20a of the MS 20 may be directly connected to the outlet 3b of the long path gas cell 3, and the outlet 30b of the front end unit 30 may be directly connected to the intake 3a of the long path gas cell 3. Downsizing of the entire combined analyzing apparatus can also be realized by making the analyzing equipment unit A smaller in these cases, as described above.

Furthermore, a length of a duct for taking a gas sample from the long path gas cell 3 into the MS 20 or from the front end unit 30 into the long path gas cell 3 may be 5 cm or shorter, for example.

Note that, in order to produce a vacuum inside the ionization unit 22 of the MS 20, a pump for evacuating the ionization unit 22 and a solenoid valve for isolating the inside of the ionization unit 22 from the inside of the long path gas cell 3 may be arranged in the case 50. In this case, the solenoid valve is mounted between the outlet 3b of the long path gas cell 3 and the intake 20a of the MS 20.

Figure 6:
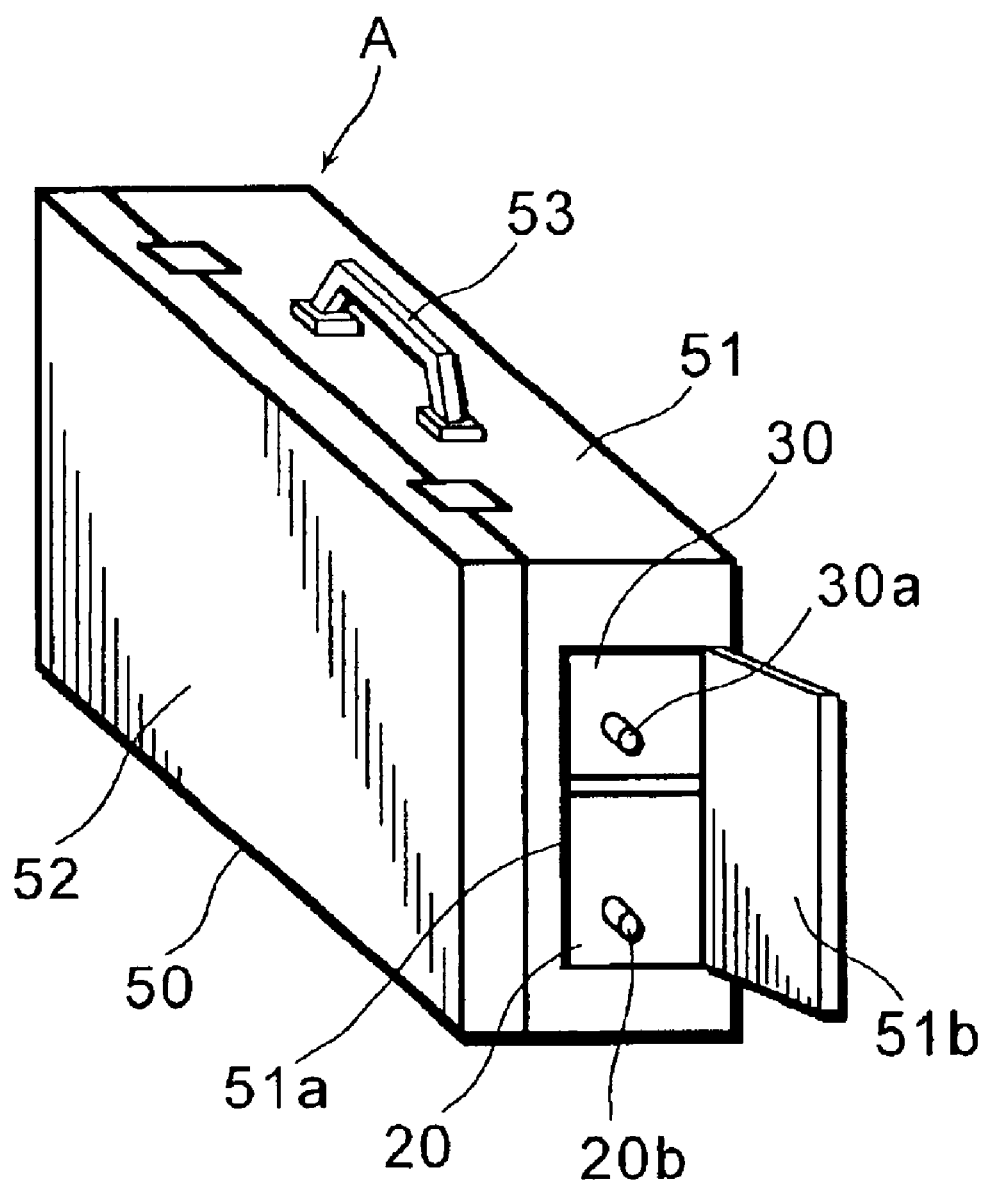
FIG. 6 is an external perspective view of the analyzing equipment unit according to the present embodiment.

FIG. 6 is an external perspective view of the analyzing equipment unit A with its lid 52 closed.

This analyzing equipment unit A is usually carried with the lid 52 of the case 50 closed, as shown in FIG. 6. When a gas sample is analyzed, only the opening/closing door 51b is opened so as to take the gas sample inside from the intake 30a of the front end unit 30 and take the gas sample outside from the outlet 20b of the MS 20. The intake 30a and the outlet 20b are exposed respectively from the opening window 51a. When the maintenance of each analyzing apparatus in the case 51 is done, the lid 52 is opened.

The combined analyzing apparatus according to the present invention has been explained above using the embodiment, but the present invention is not limited to this embodiment.

The FTIR 10 is included in the present invention, for example, but a combined gas chromatograph-Fourier transform infrared spectrophotometer (hereinafter referred to as "GC-FTIR") 100 including a gas chromatograph and a Fourier transform infrared spectrophotometer may be included instead of the FTIR 10.

Figure 7A:
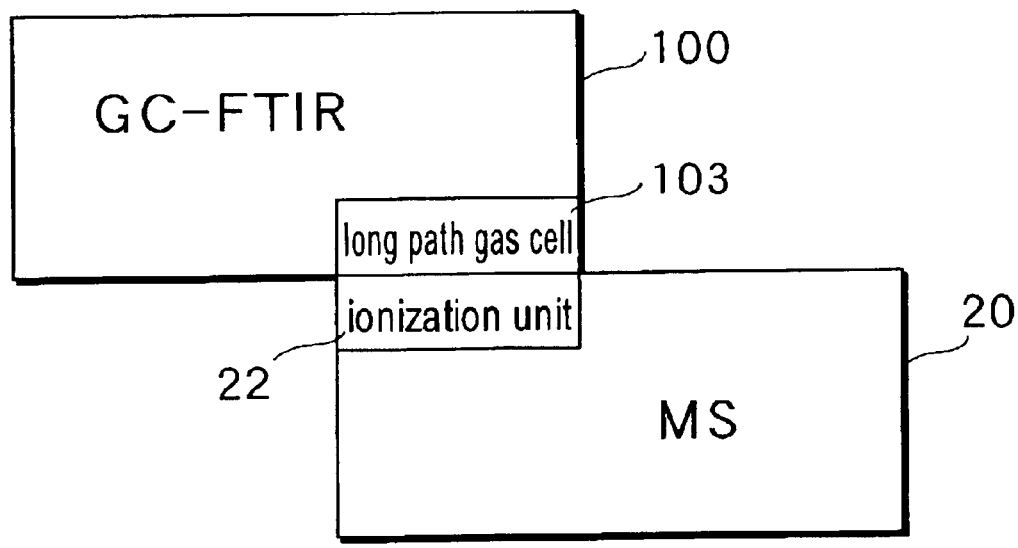
FIG. 7A is a layout of a gas chromatograph-Fourier transform infrared spectrophotometer (GC-FTIR) and a mass spectrometer (MS).

FIG. 7A shows a layout of the GC-FTIR 100 and the MS 20.

Although it was difficult to analyze a mixture of gases in the analyzing apparatus including the FTIR 10, the GC-FTIR 100 makes it possible to separate ingredients included in a gas sample for an IR analysis, and therefore, more accurate analysis of the gas sample can be realized.

Here, the GC-FTIR 100 includes a long path gas cell 103 having the same function as that of the long path gas cell 3 of the FTIR 10, and is arranged so that the long path gas cell 103 is in close contact with the ionization unit 22 of the MS 20.

Accordingly, downsizing of the entire combined analyzing apparatus can be realized by making the analyzing equipment unit A smaller, as in the case of the analyzing apparatus including the FTIR 10.

Furthermore, although the present embodiment includes the MS 20 that is a time of flight mass spectrometer, it may include a gas chromatograph-mass spectrometer (hereafter referred to as "GC-MS") instead of the MS 20.

Figure 7B:
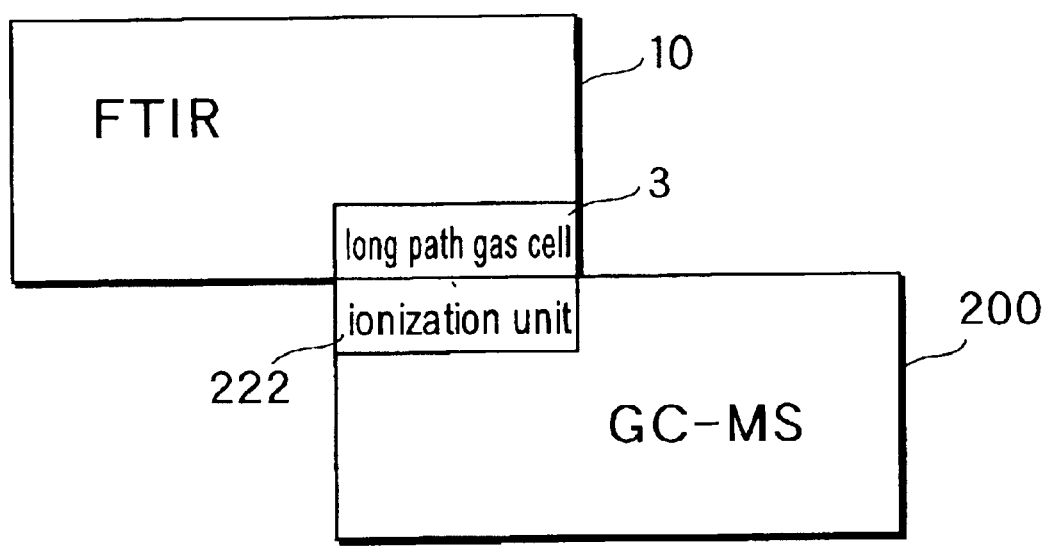
FIG. 7B is a layout of a Fourier transform infrared spectrophotometer (FTIR) and a gas chromatograph-mass spectrometer (GC-MS).

FIG. 7B is a layout of the FTIR 10 and the GC-MS 200.

The analyzing apparatus including the GC-MS 200 as shown in FIG. 7B can separate ingredients of a gas sample including many ingredients so as to make a qualitative analysis.

Here, the GC-MS 200 includes an ionization unit 222 with the same function as that of the ionization unit 22 of the MS 20, and is arranged so that the ionization unit 222 is in close contact with the long path gas cell 3 of the FTIR 10.

Accordingly, downsizing of the entire combined analyzing apparatus can be realized by making the analyzing equipment unit A smaller, as in the case of the analyzing apparatus including the MS 20.

Furthermore, an electric field mass analyzing apparatus may be included instead of the MS 20, and each ingredient of a gas sample may be ionized by a secondary ion mass spectrometry (SIMS) that ionizes an ingredient of a gas sample by applying argon ions, etc. to the gas sample.

Also, a quadrupole mass analyzing apparatus may be included instead of the MS 20. In this case, as a mass analysis can be made only by the electric field action, a high-speed scanning measurement and a high-speed switching measurement can be performed, and therefore the cost can be further reduced.

In the FTIR 10 of the present embodiment including the long path gas cell 3, a gas sample in the long path gas cell 3 is analyzed by transmitting infrared rays through the gas sample. But it may be analyzed by an attenuated total reflection (ATR) method by adding a prism or the like to the FTIR 10.

Furthermore, although a gas is analyzed in the present embodiment, a solid including a liquid and a powder may be analyzed.

When a liquid is analyzed, for example, the liquid to be analyzed is injected into the case 50 from outside, vaporized by a vaporizer which is placed in the case 50, and then analyzed by the front end unit 30, and the FTIR 10 and the MS 20. Accordingly, the scope of analysis can be widened and the usability can be improved.

Furthermore, although all the front end unit 30, and the FTIR 10 and the MS 20 make analysis as a series of operations in the present embodiment, only the FTIR 10 may analyze, or only the front end unit 30 or the MS 20 may analyze, for example.

An analysis may be made by the ATR method, for example, by adding a probe consisting of an optical crystal with its one end being projected from the case 50, instead of the above prism. The probe performs multiple reflection of infrared rays outputted from the interference unit 2 in the case 50, in the same manner as the long path gas cell 3.

When an object such as a liquid or a solid is analyzed, the end of the probe outside the case 50 is made contact with the object. Accordingly, the infrared rays repeat reflection on the inner faces of the probe, get through the inside of the case 50 to the object outside as if it were guided by the probe, is reflected by the object, repeats reflection again on the inner faces of the probe, returns to the case 50, and finally is detected by the detection unit 4.

As mentioned above, the FTIR 10 that makes the ATR analysis with the probe analyzes the object outside the case 50 without taking it into the case 50, independent of the front end unit 30 and the MS 20.

When the front end unit 30 is a photoacoustic spectroscope, the photoacoustic spectroscope may be configured for an analysis of a liquid or a solid by a so-called laser PAS (photoacoustic spectroscopy) that analyzes the object by irradiating a laser beam to the object. When the liquid or the solid is analyzed, a dedicated holder is used to fix the object onto the holder.

Furthermore, the ionization unit 22 of the MS 20 may perform ionization by an MALDI (matrix assisted laser desorption/ionization) method.

As mentioned above, the FTIR 10 makes an ATR analysis using a probe, the front end unit 30 is configured as a laser PAS, or the MS 20 performs ionization by the MALDI method, and thereby a toxin or a virus which anthrax, etc. in the air or liquid generates can be easily analyzed.

What is claimed is:

1. A combined analyzing apparatus comprising:
   Fourier transform infrared spectrophotometer operable to take a gas sample inside and analyze the gas sample based on a change of light which is transmitted through the gas sample;

a mass analyzing apparatus operable to take the analyzed gas sample from the Fourier transform infrared spectrophotometer inside and analyze a mass of an ingredient of the gas sample;

a single signal processing apparatus operable to perform digital signal processing on a signal outputted from the Fourier transform infrared spectrophotometer, and a signal outputted from the mass analyzing apparatus;

a portable case housing the Fourier transform infrared spectrophotometer, the mass analyzing apparatus, and the signal processing apparatus: and a valve, wherein the Fourier transform infrared spectrophotometer includes a cell container that is filled with the gas sample in order to transmit the light through the gas sample and an outlet for taking the gas sample outside the cell container, the mass analyzing apparatus includes an ionization unit operable to ionize the gas sample and an intake for taking the gas sample inside the ionization unit, and the outlet of the Fourier transform infrared spectrophotometer is directly connected to the intake of the mass analyzing apparatus, the valve being sandwiched between the outlet and the intake.

2. The combined analyzing apparatus according to claim 1, wherein the Fourier transform infrared spectrophotometer is a gas chromatograph Fourier transform infrared spectrophotometer.

3. The combined analyzing apparatus according to claim 1, wherein the mass analyzing apparatus is a time of flight mass spectrometer.

4. The combined analyzing apparatus according to claim 1, wherein the mass analyzing apparatus is a quadrupole mass spectrometer.

5. The combined analyzing apparatus according to claim 1, wherein the mass analyzing apparatus is a gas chromatograph mass spectrometer.

6. The combined analyzing apparatus according to claim 1, further comprising a front end analyzing apparatus housed in the portable case, the front end analyzing apparatus being operable to take the gas sample inside and analyze the gas sample before the Fourier transform infrared spectrophotometer and the mass analyzing apparatus analyze the gas sample.

7. The combined analyzing apparatus according to claim 6, wherein the front end analyzing apparatus is a photoacoustic spectroscope operable to analyze the gas sample by a photoacoustic spectroscopy.

8. The combined analyzing apparatus according to claim 6, wherein the front end analyzing apparatus is an X-ray analyzing apparatus operable to analyze an X-ray which is emitted from the gas sample.

9. The combined analyzing apparatus according to claim 6, further comprising a digital processing unit operable to perform quantitative analysis based on the signals which are outputted from the Fourier transform infrared spectrophotometer and the mass analyzing apparatus and a signal which is outputted from the front end analyzing apparatus, and display a chart indicating an analysis result by the Fourier transform infrared spectrophotometer, a chart indicating an analysis result by the mass analyzing apparatus and a chart indicating an analysis result by the front end analyzing apparatus.

10. The combined analyzing apparatus according to claim 1, further comprising a digital processing unit operable to perform quantitative analysis based on the signals which are outputted from the Fourier transform infrared spectrophotometer and the mass analyzing apparatus, and display analysis results by both the Fourier transform infrared spectrophotometer and the mass analyzing apparatus.

11. The combined analyzing apparatus according to claim 6, wherein the front end analyzing apparatus has an outlet for taking out the gas sample which has been taken inside, the Fourier transform infrared spectrophotometer has an intake for taking the gas sample inside, and the outlet of the front end analyzing apparatus is connected approximately face to face with the intake of the Fourier transform infrared spectrophotometer so that the gas sample is led from the front end analyzing apparatus straight to the mass analyzing apparatus via the Fourier transform infrared spectrophotometer without branching off.

12. The combined analyzing apparatus according to claim 1, further comprising, housed in the portable case, a photoacoustic spectroscope operable to take the gas sample inside and analyze the gas sample by a photoacoustic spectroscopy before the Fourier transform infrared spectrophotometer and the mass analyzing apparatus analyze the gas sample, wherein the signal processing apparatus is further operable to perform digital signal processing on a signal outputted from the photoacoustic spectroscope, and the photoacoustic spectroscope has an outlet for taking the gas sample outside the photoacoustic spectroscope and the Fourier transform infrared spectrophotometer has an intake for taking the gas sample inside the cell container of the Fourier transform infrared spectrophotometer, the outlet of the photoacoustic spectroscope being directly connected face to face with the intake of the Fourier transform infrared spectrophotometer.

13. The combined analyzing apparatus according to claim 12, wherein the mass analyzing apparatus has an outlet for taking the gas sample outside the mass analyzing apparatus, and the portable case has a window for exposing the outlet of the mass analyzing apparatus to the outside, and a door for opening and closing the window.

14. The combined analyzing apparatus according to claim 13, wherein the mass analyzing apparatus is a time of flight mass spectrometer.

15. The combined analyzing apparatus according to claim 14, further comprising a display apparatus operable to display, on a same screen, an infrared absorption spectrum indicating an analysis result of the Fourier transform infrared spectrophotometer and a mass spectrum indicating an analysis result of the mass analyzing apparatus, based on a processing result of the signal processing apparatus.

16. The combined analyzing apparatus according to claim 14, further comprising a display apparatus operable to display, on a same screen, an infrared absorption spectrum indicating an analysis result of the Fourier transform infrared spectrophotometer, a mass spectrum indicating an analysis result of the mass analyzing apparatus, and a concentration of each ingredient included in the gas sample analyzed by the photoacoustic spectroscope, based on a processing result of the signal processing apparatus.

17. The combined analyzing apparatus according to claim 13,
wherein the mass analyzing apparatus is a quadrupole mass spectrometer.

18. A combined analyzing apparatus comprising:
a photoacoustic spectroscope operable to take a gas sample inside and analyze the gas sample by a photoacoustic spectroscopy, the photoacoustic spectroscope having an intake for taking the gas sample inside the photoacoustic spectroscope and an outlet for taking the gas sample outside the photoacoustic spectroscope;
a Fourier transform infrared spectrophotometer operable to take the gas sample analyzed by the photoacoustic spectroscope inside and analyze the gas sample based on a change of light which is transmitted through the gas sample;
a time of flight mass spectrometer operable to take the gas sample analyzed by the Fourier transform infrared spectrophotometer inside and analyze a mass of an ingredient of the gas sample;
a single signal processing apparatus operable to perform digital signal processing on a signal outputted from the Fourier transform infrared spectrophotometer, a signal outputted from the time of flight mass spectrometer, and a signal outputted from the photoacoustic spectroscope;
a portable case housing the photoacoustic spectroscope, the Fourier transform infrared spectrophotometer, the time of flight mass spectrometer and the signal processing apparatus;
a display apparatus operable to display, on a same screen, an infrared absorption spectrum indicating an analysis result of the Fourier transform infrared spectrophotometer, a mass spectrum indicating an analysis result of the time of flight mass spectrometer, and a concentration of each ingredient included in the gas sample analyzed by the photoacoustic spectroscope, based on a processing result of the signal processing apparatus; and
a valve, wherein
the Fourier transform infrared spectrophotometer includes a cell container that is filled with the gas sample in order to transmit light through the gas sample, an intake for taking the gas sample inside the cell container, and an outlet for taking the gas sample outside the cell container,
the time of flight mass spectrometer includes an ionization unit operable to ionizes the gas sample, an intake for taking the gas sample inside the ionization unit, and an outlet for taking the gas sample outside the time of flight mass spectrometer,
the outlet of the Fourier transform infrared spectrophotometer is directly connected to the intake of the time of flight mass spectrometer, the valve being sandwiched between the outlet and the intake,
the outlet of the photoacoustic spectroscope is directly connected face to face with the intake of the Fourier transform infrared spectrophotometer, and
the portable case has a window formed on one side thereof for exposing the outlet of the time of flight mass spectrometer and the intake of the photoacoustic spectroscope, and a door for opening and closing the window.

* * * * *